United States Patent [19]

Young

[11] Patent Number: 5,725,374
[45] Date of Patent: Mar. 10, 1998

[54] COUPLER WITH CHECK VALVE FOR A DENTAL EJECTOR HOSE

[75] Inventor: Barry S. Young, Tualatin, Oreg.

[73] Assignee: Dental Components, Inc., Newberg, Oreg.

[21] Appl. No.: 617,081

[22] Filed: Mar. 18, 1996

[51] Int. Cl.⁶ .................................. A61C 17/14
[52] U.S. Cl. .................... 433/95; 604/247; 604/902
[58] Field of Search .................... 433/91, 95, 96; 604/35, 119, 247, 902

[56] References Cited

U.S. PATENT DOCUMENTS

| | | | |
|---|---|---|---|
| 2,867,213 | 1/1959 | Thomas, Jr. | 604/247 |
| 4,222,407 | 9/1980 | Ruschke et al. | 137/512.15 |
| 4,556,086 | 12/1985 | Raines | 604/247 |
| 4,859,182 | 8/1989 | Nerli | 433/80 |
| 4,966,551 | 10/1990 | Betush | 433/95 |
| 4,998,880 | 3/1991 | Nerli | 433/80 |
| 5,203,769 | 4/1993 | Clement et al. | 604/902 |
| 5,401,255 | 3/1995 | Sutherland et al. | 604/247 |
| 5,464,397 | 11/1995 | Powers, Jr. | 433/95 |
| 5,480,124 | 1/1996 | Bartlett et al. | 251/309 |

*Primary Examiner*—Ralph Lewis
*Attorney, Agent, or Firm*—James D. Givnan, Jr.

[57] ABSTRACT

A coupler is adapted for inserted engagement with a dental ejector valve and serves to couple a vacuum hose to the valve. A passageway in the coupler is closed by a flexible disk which flexes open in response to a vacuum inducted ejector system flow from a source. The disk is confined in place across the passageway by a retainer which biases the disk into engagement with a valve seat surface. The flexible disk blocks any reverse flow through the coupler as when a reduced pressure occurs from interaction of the patient's mouth with a saliva ejector.

3 Claims, 1 Drawing Sheet

COUPLER WITH CHECK VALVE FOR A DENTAL EJECTOR HOSE

BACKGROUND OF THE INVENTION

The present invention pertains generally to dental equipment for use in removing water, saliva, debris, etc. from a dental patient's mouth during treatment.

A saliva ejector is placed in the patient's mouth to pick up moisture and matter during dental work. A vacuum source draws the removed matter past a valve control and through a suction hose to a discharge point. Normally there is no reverse or back flow of removed matter back through the ejector and into the patient's mouth. In certain instances however a reverse flow can take place resulting in matter, earlier removed from a patient's mouth, being returned to the patient's mouth or the mouth of a later patient which, of course, is highly undesirable.

Saliva ejector valves, used in ejector systems, serve only to control communication of the ejector or pick up device in the mouth with a vacuum source and are not usually cycled during treatment of a patient.

SUMMARY OF THE PRESENT INVENTION

The present invention is embodied in a coupler for a vacuum hose with provision made for blocking a reverse or back flow towards a patient's mouth.

A housing of the coupler includes a flexible disk which flexes to permit a normal ejector flow toward the vacuum source. The disk is held in place by a retainer which engages the disk in a manner permitting flexure of portions of the disk in the presence of a pressure differential across the disk. The disk is highly sensitive to a range of pressure differentials to the extent that even a modest differential, resulting from interaction of the patient's mouth with the ejector device, is sufficient to cause seating of the disk to block a reverse flow. The disk retainer may also include a barb for reception of a hose end segment. A coupler housing is provided with means permitting coupler installation on an ejector valve in a quick release manner without the aid of tools.

Important objectives include the provision of a hose coupler for use in a dental ejector system to provide a check valve function in the system without altering system components other than the hose coupler; the provision of a hose coupler responsive to slight pressure differences in an ejector system to prevent any reverse or back flow toward a patient's mouth; the provision of a hose coupler wherein a resilient flexible disk is the sole moving element and permits a virtually unobstructed flow toward a vacuum source while being responsive to prevent any flow in the opposite direction.

BRIEF DESCRIPTION OF THE DRAWINGS

With continuing attention to the drawings.

DETAILED DESCRIPTION OF THE PREFERRED EMBODIMENTS

Figure 1:
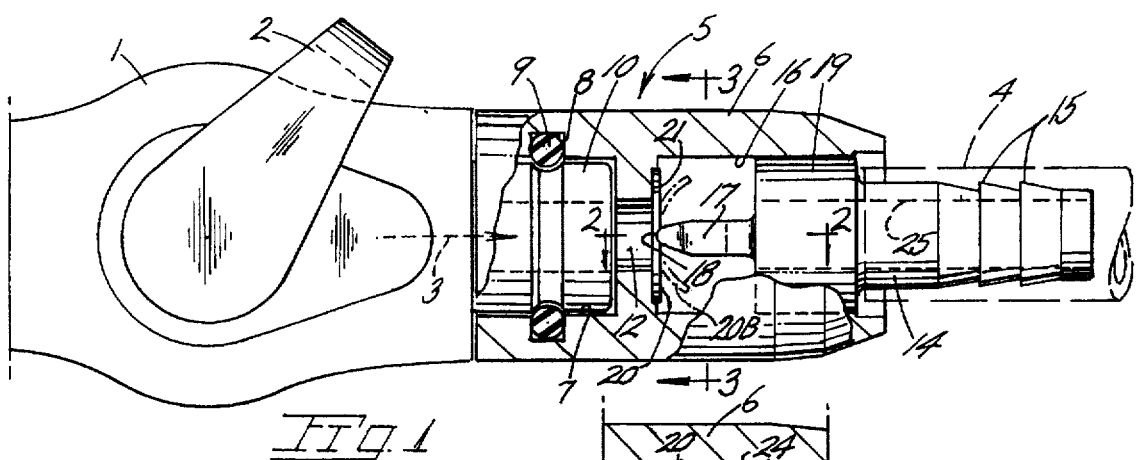
FIG. 1 is a side elevational view of an ejector valve with the present coupler in place thereon and shown in section.
Figure 2:
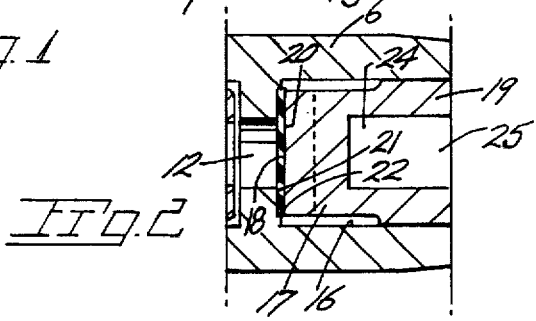
FIG. 2 is a horizontal sectional view taken downwardly along line 2—2 of FIG. 1.
Figure 3:
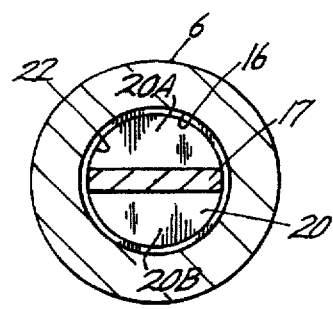
FIG. 3 is a vertical sectional view taken along line 3—3 of FIG. 1.

With continuing attention to the drawings, the reference numeral 1 indicates an ejector valve of a dental ejector system. A valve handle is at 2. During use of an ejector system a flow occurs in the direction of an arrow 3 from the patient's mouth to a source of low pressure at the unseen end of a hose 4.

The present coupler is indicated generally at 5 and includes a housing 6. At the valve engaging end of the coupler is a socket 7. A groove 8 in the coupler carries a ring 9 for engagement with a plug 10 of the ejector valve. Socket 7 communicates with a passageway 12 of the housing.

A connector at 14 is provided with annular ridges 15, sometimes termed barbs, for inserted engagement with suction hose 4. Connector 14 includes a head 19 for inserted snug engagement with a bore 16 in housing 6. To render such engagement more or less permanent an adhesive may be utilized such as the adhesive sold under the registered trademark LOCKTITE. Projecting from head 19 and integral therewith is a retainer 17 which terminates in an elongate end wall 18.

A disk at 20 is of an elastomeric material and in a non-flexed condition abuts an annular valve seat 21 located about passageway 12 of the housing. The seat is outwardly defined by a housing shoulder 22 which aids in retention of the disk. One suitable disk for present purposes is formed of an elastomeric material sold under the trademark VITON, having a 50 durometer rating and a thickness of 0.017 inches.

Elongate end wall 18 is preferably a curved surface, as viewed in side elevation in FIG. 1, to promote flexing of diametrically opposed segments 20A-20B with minimum abrasion of the disk. Wall 18 engages a diametrical area of the disk and urges end portions of the area against seat 21 which, along with shoulder 22 of housing 6, retains the disk in place.

During normal functioning of the dental ejector system, the flexed segments 20A-20B shown in broken lines in FIG. 1, will maintain an open position for the passage of water and particles through an open area 24 to disk retainer 14 and subsequently along a lengthwise opening 25 of the retainer and into hose 4. In those instances where the saliva ejector, in place in the patient's mouth, is subjected to a momentary pressure drop from interaction of the mouth with the ejector, a reverse or back flow is prevented by the immediate and full seating of disk 20 on seat 21.

While I have shown but one embodiment of the invention, it will be apparent to those skilled in the art that the invention may be embodied still otherwise without departing from the spirit and scope of the invention.

Having thus described the invention, what is desired to be secured by a Letters Patent is:

I claim:

1. A coupler with check valve for attaching a vacuum hose to a dental ejector valve, said coupler comprising:

a tubular housing having a first end defining a socket for connection to the dental ejector valve, a second end for connection to the vacuum hose, said housing defining a passageway between said first and second ends, a ring in said socket for engagement with the ejector valve, said housing having an annular valve seat spaced from said socket and said second end, said annular valve seat encircling said passageway, a tubular vacuum hose connector having first and second ends, said connector first end having an enlarged head insertably engaged with said second end of said housing, said vacuum hose connector second end adapted to be connected to said vacuum hose, a flexible disk in said housing in place on and cooperable with said valve seat to close the passageway in said housing when said disk is in a non-flexed condition, a disk engaging means extending axially from said head of the vacuum hose connector for biasing portions of the disk into engagemment with the housing valve seat, and said disk having segments displaceable from said seat in response to a fluid flow in one direction through said passageway, said disk in sealing engagement with said valve seat in the absence of said fluid flow to block any fluid flow in a direction opposite to said one direction.

2. The invention claimed in claim 1 wherein said disk engaging means includes an elongate end wall coterminous with the periphery of said disk, said elongate end wall is a curved surface to facilitate flexure of the disk.

3. In combination, a dental ejector valve having an outlet, a coupler serving to connect a vacuum hose to said ejector valve and preventing backflow of a fluid from the hose to the ejector valve in the absence of a vacuum induced flow, said coupler comprising, a tubular housing having a first end defining a socket for connection to the dental ejector valve, a second end for connection to the vacuum hose, said housing defining a passageway between said first and second ends, a ring in said socket for engagement with the ejector valve, said housing having an annular valve seat spaced from said socket and said second end, said annular valve seat encircling said passageway, a tubular vacuum hose connector having first and second ends, said connector first end having an enlarged head insertably engaged with said second end of said housing, said vacuum hose connector second end adapted to be connected to said vacuum hose, a flexible disk in said housing in place on and cooperable with said valve seat to close the passageway in said housing when said disk is in a non-flexed condition, a disk engaging means extending axially from said head of the vacuum hose connector for biasing portions of the disk into engagement with the housing valve seat, and said disk having segments displaceable from said seat in response to a fluid flow in one direction through said passageway, said disk in sealing engagment with said valve seat in the absence of said fluid flow to block any fluid flow in a direction opposite to said one direction.

* * * * *